US010213397B2

(12) United States Patent
Wilcox et al.

(10) Patent No.: US 10,213,397 B2
(45) Date of Patent: Feb. 26, 2019

(54) MICROTUBULE POLYMERIZATION MODULATORS FOR TREATING LMNA-RELATED DILATED CARDIOMYOPATHY

(71) Applicants: Northwestern University, Evanston, IL (US); Creighton University, Omaha, NE (US)

(72) Inventors: Jane Elizabeth Wilcox, Oak Park, IL (US); Joshua D. Prenosil, Omaha, NE (US)

(73) Assignees: Northwestern University, Evanston, IL (US); Creighton University, Omaha, NE (US)

(*) Notice: Subject to any disclaimer, the term of this patent is extended or adjusted under 35 U.S.C. 154(b) by 0 days.

(21) Appl. No.: 15/850,085

(22) Filed: Dec. 21, 2017

(65) Prior Publication Data
US 2018/0169040 A1 Jun. 21, 2018

Related U.S. Application Data

(60) Provisional application No. 62/437,170, filed on Dec. 21, 2016.

(51) Int. Cl.
A61K 31/165 (2006.01)
A61P 9/00 (2006.01)
A61K 45/06 (2006.01)

(52) U.S. Cl.
CPC ............ A61K 31/165 (2013.01); A61K 45/06 (2013.01); A61P 9/00 (2018.01)

(58) Field of Classification Search
None
See application file for complete search history.

(56) References Cited

U.S. PATENT DOCUMENTS

| | | |
|---|---|---|
| 7,601,758 B1 | 10/2009 | Davis |
| 7,619,004 B1 | 11/2009 | Davis |
| 7,820,681 B1 | 10/2010 | Davis |
| 7,906,519 B2 | 3/2011 | Davis |
| 7,915,269 B2 | 3/2011 | Davis |
| 7,935,731 B2 | 5/2011 | Davis |
| 7,964,647 B2 | 6/2011 | Davis |
| 7,964,648 B2 | 6/2011 | Davis |
| 7,981,938 B2 | 7/2011 | Davis |
| 8,093,296 B2 | 1/2012 | Davis |
| 8,093,297 B2 | 1/2012 | Davis |
| 8,093,298 B2 | 1/2012 | Davis |
| 8,097,655 B2 | 1/2012 | Davis |
| 8,415,395 B1 | 4/2013 | Davis et al. |
| 8,415,396 B1 | 4/2013 | Davis et al. |
| 8,440,721 B2 | 5/2013 | Davis |
| 8,440,722 B2 | 5/2013 | Davis |
| 2015/0250762 A1 | 9/2015 | Worman |

OTHER PUBLICATIONS

Deftereos et al., Journal of the American College of Cardiology (2013), 62(2), pp. 1817-1825.*
Saji et al., The Tohoku Journal of Experimental Medicine (2007), 213(2), pp. 139-148.*
Arbustini et al. 2002, "Autosomal dominant dilated cardiomyopathy with atrioventricular block: a lamin A/C defect-related disease," J Am Coll Cardiol, Mar. 20;39(6):981-90.
Botto et al., "A novel LMNA mutation (R189W) in familial dilated cardiomyopathy: evidence for a 'hot spot' region at exon 3: a case report," Cardiovascular Ultrasound, 2010 (8):9.
Brodsky, G.L., "Lamin A/C Gene Mutation Associated With Dilated Cardiomyopathy With Variable Skeletal Muscle Involvement," Circulation, Feb. 8, 2000, vol. 101, Issue 5.
Kärkkäinen et al. 2006, "Novel mutations in the lamin A/C gene in heart transplant recipients with end stage dilated cardiomyopathy," Heart, Apr.;92(4): 524-526.
Lu et al., "An Overview of Tubulin Inhibitors That Interact with the Colchicine Binding Site," Pharm Res., Nov. 2012; 29 (11): 2943-2971.
Parks et al. 2008; "Lamin A/C mutation analysis in a cohort of 324 unrelated patients with idiopathic or familial dilated cardiomyopathy," Am Heart J, Jul.;(156(1): 161-9.
Perrot et al. 2009, "Identification of mutational hot spots in LMNA encoding lamin A/C in patients with familial dilated cardiomyopathy," Basic Res Cardiol, Jan.; 104(1): 90-9.
Zhang et al., "Microtubule-Mediated Defects in Junctophilin-2 Trafficking Contribute to Myocyte Transverse-Tubule Remoding and Ca2+ Handling Dysfunction in Heart Failure," Circulation, Molec Cardiol, Apr. 29, 2014, pp. 1742-1750.
International Search Report and Written Opinion for PCT/US2017/067812 dated Apr. 12, 2018.
Chatterjee, et al., "Vincristine attenuates doxorubicin cardiotoxicity", Biochem Biophys Res Commun., 2008, vol. 373, No. 4, pp. 555-560.
Gultekin, et al., "Microtubule inhibition therapy by colchicine in severe myocarditis especially caused by Epstein-Barr and cytomegalovirus co-infection during a two-year period: a novel therapeutic approach", J Pak Med Assoc., 2014, vol. 64, No. 12, pp. 1420-1423.
Henningsen, et al., "Ventricular tachyarrhythmias in patients with cardiomyopathy", Ugeskr Laeger, 2008, vol. 170, No. 25, pp. 2238-2242.

(Continued)

Primary Examiner — Brian J Davis
(74) Attorney, Agent, or Firm — Andrus Intellectual Property Law, LLP

(57) ABSTRACT

Disclosed are methods and pharmaceutical compositions for treating cardiomyopathies. The disclosed methods and pharmaceutical compositions may be used for treating lamin A/C (LMNA)-related dilated cardiomyopathies (DCM) in a subject in need thereof. The disclosed methods may utilize and the disclosed pharmaceutical compositions may include an effective amount of a modulator of microtubule polymerization such as colchicine.

17 Claims, No Drawings

(56) References Cited

OTHER PUBLICATIONS

Puckelwartz, et al., "Gene expression, chromosome position and lamin A/C mutations", Nucleus, 2011, vol. 2, No. 3, pp. 162-167.
Cocco, Giuseppe; Chu, David C.C.; Pandolti, Stefano (2010). "Colchicine in clinical medicine. A guide for internists". European Journal of Internal Medicine. 21 (6): 503-8. PMID 21111934. doi:10.1016/j.ejim.2010.09.010.
Goldfinger SE. Colchicine for familial Mediterranean fever. New England Journal of Medicine. 1972;287(25):p. 1302.
Larrieu et al, Chemical Inhibition of NAT10 Corrects Defects of Laminopathic Cells. Science. 2014:344; 527-32.
Vitale A, Rigante D, Lucherini OM, et al; Biological treatments: new weapons in the management of monogenic autoinflammatory disorders. Mediators Inflamm. 2013 2013:939847. doi: 10.1155/2013/939847. Epub Jul. 21, 2013.

* cited by examiner

MICROTUBULE POLYMERIZATION MODULATORS FOR TREATING LMNA-RELATED DILATED CARDIOMYOPATHY

CROSS-REFERENCE TO RELATED PATENT APPLICATIONS

This application claims the benefit of priority under 35 U.S.C. § 119(e) to U.S. Provisional Application No. 62/437,170, filed on Dec. 21, 2016, the content of which is incorporated herein by reference in its entirety.

BACKGROUND

The field of the invention relates to the use of agents that modulate microtubule polymerization for treating cardiomyopathy. In particular, the field of the invention relates to the use of colchicine for treating LMNA-related dilated cardiomyopathy.

SUMMARY

Disclosed are methods and pharmaceutical compositions for treating cardiomyopathies. The disclosed methods and pharmaceutical compositions may be used for treating lamin A/C (LMNA)-related dilated cardiomyopathies (DCM) in a subject in need thereof. The disclosed methods may utilize and the disclosed pharmaceutical compositions may include an effective amount of a modulator of microtubule polymerization such as colchicine or a pharmaceutical salt or solvate thereof.

DETAILED DESCRIPTION

The present invention is described herein using several definitions, as set forth below and throughout the application.

Definitions

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the term "subject," "patient," and "individual" may be used interchangeably and may refer to human and non-human animals. A subject in need thereof may include a subject having or at risk for experiencing cardiomyopathy including dilated cardiomyopathy (DCM), and in particular a familial DCM such as LMNA-related DCM.

As is known in the art, DCM is often a genetic form of heart disease which occurs when cardiac muscle becomes stretched in a chamber of the heart (left ventricle) causing the chamber to become enlarged or "dilated." The dilated chamber is unable to pump blood as efficiently as a normal-size chamber, and as a result, the cardiac muscle tries to increase the amount of blood being pumped through the heart. This often results in all four chambers of the heart becoming dilated. As the chambers become dilated, the cardiac muscle that forms the chambers becomes increasing thin and weakened and less able to pump blood. Over time, DCM results in heart failure, which is a clinical syndrome that occurs when the heart muscle is weakened and cannot pump enough blood to meet the body's needs for blood and oxygen. A diagnosis of heart failure is associated with high risk of mortality, with average 5 year survival rates of 50% at the time of initial diagnosis.

A patient may have DCM for many years prior to symptoms developing. Symptoms typically begin in mid-adulthood, but may occur at any time from infancy to late adulthood. Symptoms of DCM may include an irregular heartbeat or arrhythmia, shortness of breath or dyspnea, extreme tiredness or fatigue, fainting episodes or syncope, and swelling of extremities such as the legs and feet. In some unfortunate cases, the first sign of DCM is sudden cardiac arrest.

It has been estimated that ~750,000 people in the United States have DCM. Up to half of these cases are inherited/familial DCM, which is a genetic form of the disease. Mutations in more than 30 genes have been found to cause familial DCM, and these genes generally encode proteins that are found in cardiac muscle cells (i.e., cardiomyocytes). Many of these proteins play important roles in the contraction of cardiac muscle through association with cell structures called "sarcomeres," which are the basic units of muscle contraction and comprise proteins that generate the mechanical force needed for muscles to contract. Other proteins associated with familial DCM make up the structural framework or "cytoskeleton" of cardiomyocytes. The remaining proteins associated with familial DCM regulate biological processes within cardiomyocytes to ensure proper functioning.

One gene associated with familial DM is the lamin A/C gene or "LMNA." The LMNA gene is located on chromosome 1, NC_000001.11 (156082546 . . . 156140089) (which entry and nucleic acid sequence of the LMNA gene is incorporate herein by reference in its entirety). The LMNA gene provides instructions for making several slightly different proteins called lamins. The two major proteins produced from LMNA are lamin A and lamin C, which are made in most cells of the body. Lamin A is 664 amino acids in length and lamin C is 572 amino acids in length, and lamin A and lamin C are identical from amino acids 1-566. The amino acid sequence of lamin A is provided as SEQ ID NO:1 and the amino acid sequence of lamin C is provided as SEQ ID NO:2.

Lamin A and lamin C are structural proteins which are called "intermediate filament proteins" that provide stability and strength to cells. In particular, lamin A and lamin C are scaffolding components of the nuclear envelope, which is a structure that surrounds the nucleus in cells. Specifically, lamin A and lamin C are located in the nuclear lamina, which is a mesh-like layer of intermediate filaments and other proteins that is attached to the inner membrane of the nuclear envelope. The nuclear envelope regulates the movement of molecules into and out of the nucleus, and researchers believe that the nuclear envelope may play a role in regulating gene expression. Many mutations that change the amino acid sequences of lamin A and lamin C have been shown to be associated with familial DCM. These cases of familial DCM may be referred to as "LMNA-related DCM." (See, e.g., Botto et al., "A novel LMNA mutation (R189W) in familial dilated cardiomyopathy: evidence for a 'hot spot' region at exon 3: a case report," Cardiovascular Ultrasound, 2010 (8):9; Perrot et al. 2009, "Identification of mutational hot spots in LMNA encoding lamin A/C in patients with familial dilated cardiomyopathy," *Basic Res Cardiol, January;* 104(1): 90-9; and Brodsky, G. L., "Lamin A/C Gene Mutation Associated With Dilated Cardiomyopathy With Variable Skeletal Muscle Involvement," Circulation, Feb. 8, 2000, Volume 101, Issue 5; the contents of which are incorporated herein by reference in their entireties).

As such, disclosed herein are methods and pharmaceutical compositions for treating LMNA-related DCM and/or symptoms thereof in a subject in need thereof. The methods utilize and the pharmaceutical compositions include an effective amount of a modulator of microtubule polymerization for treating the LMNA-related DCM and/or symptoms thereof.

Suitable subjects for the disclosed methods include, but are not limited to, subjects having an LMNA-related DCM as known in the art. Genetic mutations present in subjects for the disclosed methods may include mutations in the LMNA gene (full sequence at chromosome 1, NC_000001.11 (156082546 . . . 156140089). Mutations in the LMNA gene may include, deletions, substitutions, and insertions. Mutations may include, but are not limited to a single nucleotide deletion at nucleotide 959 and/or a four base pair insertion at 1,713 cDNA. Mutations within LMNA gene may later the amino acid sequence of lamin A and/or the amino acid sequence of lamin C, for example by deletion, substitution, or insertion in the amino acid sequence of lamin A and/or the amino acid sequence of lamin C. Mutations that alter the amino acid sequence of lamin A and/or that alter the amino acid sequence of lamin C may include, but are not limited to K97E, E111X, E161K, R1S9W. R190Q, R190W, E203V, K219T, E317K, R644C.

The disclosed mutations in the LMNA gene may disrupt one or more functions of lamin A and/or lamin C. In some embodiments, the disclosed mutations in the LMNA gene disrupt the formation and/or function of the Links the Nucleus to the Cytoplasm (LINC) complex.

Subjects suitable for the disclosed methods may include subject exhibiting a cardiac conduction disease. In some embodiments, the subject is exhibiting a cardiac conduction disease selected from sinus atrial node disease, atrial dysrhythmias, atrioventricular heart block, ventricular tachyarrhythmias, and combinations thereof. Preferably, the disclosed methods treat the cardiac conduction system disease.

The disclosed methods utilize and the disclosed pharmaceutical composition includes a modulator of microtubule polymerization. As used herein, the term "modulation" may include "inhibition" and/or "promotion." In some embodiments, the disclosed modulators of microtubule polymerization inhibit microtubule polymerization. In other embodiments, the disclosed modulators of microtubule polymerization promote microtubule depolymerization. Suitable modulators of microtubule polymerization for the disclosed methods and pharmaceutical compositions may include, but are not limited to colchicine, combretastatins, 2-methoxyestradiol, methoxy benzenesulfonamides (E7010), vinblastine, vincristine, vinflunine, crytophycin 52, halichondrins, dolastatin 10, dolastatin 15, hemiasterlin A, and hemiasterlin B.

Modulators of microtubule polymerization for use in the disclosed methods and pharmaceutical compositions may include, but are not limited to, agents that bind to tubulin and modulate microtubule polymerization. In some embodiments, the modulator of microtubule polymerization binds tubulin at the colchicine domain and inhibits tubulin polymerization. Tubulin inhibitors that interact with the colchicine binding site are known in the art. (See Lu et al., "An Overview of Tubulin Inhibitors That Interact with the Colchicine Binding Site," *Pharm Res.,* 2012 November; 29(11): 2943-2971, the content of which is incorporated herein by reference in its entirety). Tubulin inhibitors that interact with the colchicine binding site may include, but are not limited to colchicine, ZD6126, CA-4 and its analogs, CA-4P, Oxi4503, AVE8062, Phenstatin, CC-5079, Podophyllotoxin, Steganacin, Nocodazole, Curacin A, 2-ME, ENMD-1198, ABT-751, T128067, BCN-105P, Indibulin (D-24851, ZI0301), EPC2407 (Crolibulin), MPE-0441138, MPC-6827, CYT997, MN-029, CI-980, CP-248, CP 461, TN16, indole-, quinolone-, and thiophen-based colchicine binding site inhibitors, chalcone-based inhibitors, sulfonanilide-based compounds, desmosdumotins and their analogs, diketopiperazine-based compounds, antracenone-based compounds, chromene-based compounds. (See id.).

A modulator of tubulin polymerization that is particular suited for the disclosed methods and pharmaceutical compositions is colchicine having the following structure:

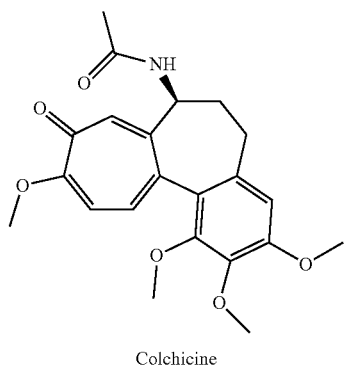

Colchicine

Derivatives of colchicine may be utilized in the disclosed pharmaceutical compositions and methods for treating lamin A/C (LMNA)-related dilated cardiomyopathy (DCM) in a subject in need thereof. Derivatives of colchicine may include, but are not limited to salts, solvates, and alkyl esters thereof.

Colchicine is a toxic natural product and metabolite of plants from the genus *Colchicum* and in particular *Colchicum autumnale* or autumn *crocus*. Colchicine is approved and marketed for treating gout under the tradename "Colcrys™" (Takeda Pharms USA) and a generic version also is available (Prasco Laboratories). Colcrys™ brand colchicine and its generic counterpart are sold as a 0.6 mg coated tablet. The recommended dose of Colcrys™ brand colchicine for treatment of a gout flare is 1.2 mg (two tablets) at the first sign of the flare followed by 0.6 mg (one tablet) one hour later. Higher doses have not been found to be more effective. Other methods for administering Colcrys™ brand colchicine, either alone or together with an ancillary medicament, to treat gout, familial Mediterranean fever, pericarditis, Behçet's disease, and atrial fibrillation are known in the art. (See, e.g., U.S. Pat. Nos. 8,440,722; 8,440,721; 8,415,396; 8,415,395; 8,097,655; 8,093,298; 8,093,297; 8,093,296; 7,981,938; 7,964,648; 7,964,647; 7,935,731; 7,915,269; 7,906,519; 7,820,681; 7,619,004; and 7,601,758; the contents of which are incorporated herein by reference in their entireties). In some embodiments of the disclosed methods for treating LMNA-related DCM and/or symptoms thereof in a subject in need thereof, colchicine may be administered similarly as colchicine and/or ancillary agents are administered to treat gout, familial Mediterranean fever, pericarditis, Behçet's disease, and atrial fibrillation. (See id.).

In other embodiments of the disclosed methods for treating LMNA-related DCM and/or symptoms thereof in a subject in need thereof, colchicine may be administered the same or differently than colchicine and/or ancillary agents are administered to treat gout, familial Mediterranean fever, and/or other diseases. For example, colchicine may be administered in the disclosed methods for treating LMNA-related DCM and/or symptoms thereof in a subject in need thereof at doses that are higher than doses of colchicine utilized for treating gout, familial Mediterranean fever, and/or other diseases.

In some embodiments of the disclosed methods, colchicine may be administered at a dose of at least about 0.3 mg, 0.6 mg, 0.9 mg, 1.2 mg, 1.5 mg, 1.8 mg, 2.1 mg, 2.4 mg, 2.7 mg, 3.0 mg, 3.3 mg, 3.6 mg, 3.9 mg, 4.2 mg, 4.5 mg, 4.8 mg, 5.1 mg, 5.4 mg, 5.7 mg, or 6.0 mg at a frequency of about once, twice, or three times per day; or colchicine may be administered at a dose of no more than about 0.3 mg, 0.6 mg, 0.9 mg, 1.2 mg, 1.5 mg, 1.8 mg, 2.1 mg, 2.4 mg, 2.7 mg, 3.0 mg, 3.3 mg, 3.6 mg, 3.9 mg, 4.2 mg, 4.5 mg, 4.8 mg, 5.1 mg, 5.4 mg, 5.7 mg, or 6.0 mg at a frequency of about once, twice, or three times per day; or colchicine may be administered within a dose range bounded by any of the foregoing values (e.g., 0.6 mg-1.2 mg, once daily, twice daily, or thrice daily). In some embodiments of the disclosed methods, colchicine may be administered at a dosage level of at least about 0.005 mg/kg body mass, 0.01 mg/kg body mass, 0.02 mg/kg body mass, 0.05 mg/kg body mass, 0.1 mg/kg body mass, 0.2 mg/kg body mass, 0.5 mg/kg body mass, at a frequency of about once, twice, or three times per day; or at a dosage level of no more than about 0.005 mg/kg body mass, 0.01 mg/kg body mass, 0.02 mg/kg body mass, 0.05 mg/kg body mass, 0.1 mg/kg body mass, 0.2 mg/kg body mass, 0.5 mg/kg body mass at a frequency of about once, twice, or three times per day; or colchicine may be administered within a dose level range bounded by any of the foregoing values (e.g., 0.005-0.02 mg/kg body mass, once daily or twice daily or thrice daily).

Colchicine is known to exhibit negative side-effects such as gastrointestinal disorders and diarrhea. In the disclosed methods, preferably colchicine is administered at a dose and/or dosage level that does not result in gastrointestinal disorders and diarrhea. In some embodiments, colchicine may be administered with an ancillary medicament that ameliorates and/or prevents gastrointestinal disorders and diarrhea that result as a negative side-effect of colchicine.

In the disclosed methods for treating LMNA-related DCM, a modulator of tubulin polymerization (e.g., colchicine) is administered to a subject in need thereof. In some embodiments, the subject may be administered a second agent for treating LMNA-related DCM and/or the symptoms thereof. Suitable second agents may include, but are not limited to an angiotensin converting enzyme (ACE) inhibitor, a beta blocker, an anti-aldosterone agent, and combinations thereof. The second agents may be administered, before, concurrently with, and/or after the modulator of tubulin polymerization. In the disclosed methods for treating LMNA-related DCM, the subject in need thereof may be further treated by implanting in the subject an implantable cardioverter-defibrillator (ICD).

ILLUSTRATIVE EMBODIMENTS

The following embodiments are illustrative and should not be interpreted as limiting the scope of the claimed subject matter.

Embodiment 1

A method for treating lamin A/C (LMNA)-related dilated cardiomyopathy (DCM) in a subject in need thereof, the method comprising administering an effective amount of a modulator of microtubule polymerization.

Embodiment 2

The method of embodiment 1, wherein the LMNA-related DCM is associated with one or more mutations in LMNA selected from K97E, E111X, E161K, R189W, R190Q, R190W, E203V, K219T, E317K, R644C, a single nucleotide deletion at nucleotide 959, and a four base pair insertion at 1,713 cDNA.

Embodiment 3

The method of embodiment 1 or 2, wherein the LMNA-related DCM is associated with one or more mutations in LMNA that disrupt formation or function of the Links the Nucleus to the Cytoplasm (LINC) complex.

Embodiment 4

The method of any of embodiments 1-3, wherein the subject having lamin A/C (LMNA)-related dilated cardiomyopathy (DCM) is exhibiting a cardiac conduction system disease selected from sinus atrial node disease, atrial dysrhythmias, atrioventricular heart block, ventricular tachyarrhythmias, and combinations thereof, and the method treats the cardiac conduction system disease.

Embodiment 5

The method of any of embodiments 1-4, wherein the modulator of microtubule polymerization is an inhibitor of microtubule modulation.

Embodiment 6

The method of embodiment 5, wherein the inhibitor of microtubule polymerization is selected from the group consisting of colchicine, combretastatins, 2-methoxyestradiol, methoxy benzenesulfonamides (E7010), vinblastine, vincristine, vinflunine, crytophycin 52, halichondrins, dolastatin 10, dolastatin 15, hemiasterlin A, and hemiasterlin B.

Embodiment 7

The method of any of embodiments 1-6, wherein the inhibitor of microtubule polymerization binds tubulin at the colchicine domain.

Embodiment 8

The method of any of embodiments 1-5, wherein the modulator of microtubule polymerization is colchicine or a pharmaceutical salt or solvate thereof.

Embodiment 9

The method of embodiment 8, wherein the colchicine is administered at a dose of at least about 0.3 mg, 0.6 mg, 0.9 mg, 1.2 mg, 1.5 mg, 1.8 mg, 2.1 mg, 2.4 mg, 2.7 mg, 3.0 mg, 3.3 mg, 3.6 mg, 3.9 mg, 4.2 mg, 4.5 mg, 4.8 mg, 5.1 mg, 5.4 mg, 5.7 mg, or 6.0 mg at a frequency of about once, twice, or three times per day.

Embodiment 10

The method of embodiment 8 or 9, wherein the colchicine is administered at a dosage level of at least about 0.005 mg/kg body mass, 0.01 mg/kg body mass, 0.02 mg/kg body mass, 0.05 mg/kg, 0.1 mg/kg, 0.2 mg/kg body mass, at a frequency of about once, twice, or three times per day.

Embodiment 11

The method of any of the foregoing embodiments, further comprising administering to the subject an agent selected from the group consisting of an angiotensin converting enzyme (ACE) inhibitor, a beta blocker, an anti-aldosterone agent, and combinations thereof.

Embodiment 12

The method of any of the foregoing embodiments, further comprising implanting in the subject an implantable cardioverter-defibrillator (ICD).

EXAMPLES

The following Examples are illustrative and are not intended to limit the scope of the claimed subject matter.

Example 1—Colchicine for LMNA-Related Dilated Cardiomyopathy

Abstract

LMNA-related dilated cardiomyopathy (DCM) is a genetic disorder that is inherited dominantly. It has been estimated that LMNA-related DCM affects at least 80,000 people in the United States alone, although the exact prevalence of LMNA-related DCM is unknown because many patients with DCM do not undergo genetic testing. The natural history of cardiac disease associated with LMNA-related cardiomyopathy is progress, and many patients need a heart transplant or experience sudden cardiac death. Based on our review of basic scientific research, we decided to try a novel treatment for LMNA-related DCM using colchicine as a therapeutic on a patient. Colchicine is approved for use in treating gout. However, we used higher doses than typically used for gout in treating LMNA-related DCM my patient. My patient has had a dramatic recovery and has experienced no negative side effects.

Application

The applications of the disclosed technology may include, but are not limited to: (a) treatment for individuals affected by LMNA dilated cardiomyopathy; (b) potential treatments for other genetic cardiomyopathies that affect the cytoskeleton, as well as skeletal muscle disorders and dystrophies that also are caused by LMNA mutations.

Advantages

Patients with LMNA-related DCM generally do not respond to existing medical therapy for heart failure. The disclosed technology may be utilized to treat these non-responding patients.

Patient with LMNA-related DCM often experience sudden death from cardiac rhythm disorders. The disclosed technology may be utilized to reduce fatality in these patients having cardiac rhythm disorders.

There currently is no drug that is approved to recover function in hearts affected by LMNA-related DCM or to reduce the burden of arrhythmia in patients with LMNA-related DCM. The disclosed technology may be utilized to recover heart function and reduce the burden of arrhythmia in patient with LMNA-related DCM Technical Description The frequency of LMNA-related DCM in persons with DCM of unknown cause (also referred to as idiopathic dilated cardiomyopathy (IDC)) ranges from 5% to 10% of familial DCM and 2% to 5% of non-familial DCM. (See Arbustini et al. 2002, "Autosomal dominant dilated cardiomyopathy with atrioventricular block: a lamin A/C defect-related disease," *J Am Coll Cardiol*, March 20; 39(6):981-90; Kärkkäinen et al. 2006, "Novel mutations in the lamin A/C gene in heart transplant recipients with end stage dilated cardiomyopathy," *Heart, April*; 92(4): 524-526; Parks et al. 2008; "Lamin A/C mutation analysis in a cohort of 324 unrelated patients with idiopathic or familial dilated cardiomyopathy," *Am Heart J*, July; (156(1): 161-9; and Perrot et al. 2009, "Identification of mutational hot spots in LMNA encoding lamin A/C in patients with familial dilated cardiomyopathy," *Basic Res Cardiol*, January; 104(1): 90-9).

The lamina proteins are part of the "LINC" complex that Links the Nucleus to the Cytoplasm. In addition to lamins A and C, mutations in other members of the LINC complex cause cardiomyopathy, including emerin, nesprin-1, and nesprin-2. Stress signals in the cytoplasm are hypothesized to act on the LINC complex to affect gene expression in the nucleus. Chromatin mislocalization occurs concomitant with changes in gene expression, suggesting that the spatial organization of chromatin may be important for disease pathogenesis. (See also Larrieu et al., "Chemical Inhibition of NAT10 Corrects Defects of Laminopathic Cells," *Science*, Vol. 344, 2 May 2014, pages 527-532). Together, these data indicate that a functional LINC complex is critical for the heart to properly respond to constant mechanical stress, potentially by regulating gene expression or other nuclear functions. In addition, T-tubule remodeling has been shown to be associated with cardiac dysfunction. (See Zhang et al., "Microtubule-Mediated Defects in Junctophilin-2 Trafficking Contribute to Myocyte Transverse-Tubule Remoding and $Ca^{2+}$ Handling Dysfunction in Heart Failure," *Circulation, Molec Cardiol*, Apr. 29, 2014, pages 1742-1750).

Example 2—Treatment of Patient Diagnosed with LMNA-Related Dilated Cardiomyopathy (DCM)

In August of 2013 patient JP was diagnosed with LMNA-related DCM, also known as "cardiac laminopathy," an inherited degenerative cardiac disorder characterized by left ventricular dilation, arrhythmia, and cardiac enlargement. It is a subset of "non-ischemic cardiomyopathy."

The patient worked as a college professor and the patient's condition worsened throughout the 2013-14 school year. The patient was heading toward long-term disability due to fatigue, shortness of breath and palpitations, all due to his progressive heart failure. In October, an implantable defibrillator was placed in the patient's chest, and the patient was hospitalized twice for cardiac arrhythmias (i.e., once for excessive premature ventricular contractions or TVCs', and once for cardiac resynchronization for atrial fibrillation). Because conventional heart failure therapy appeared unsuccessful at ameliorating disease effects, the patient undertook a comprehensive review of literature on laminopathy to find a novel treatment.

In June 2014, the patient began experiencing PVC-burden cardiomyopathy, a secondary myopathy caused by a heavy premature ventricular contraction (PVC) load. His PVCs were measured at 52,000 over a 48-hour holter-monitor. Given his deteriorating condition, now with NYHA class III heart failure, he sought care at Northwestern University's Bluhm Cardiovascular Institute in Chicago with Dr. Jane Wilcox.

Dr. Wilcox adjusted the patient's existing medication regimen to reflect best practice for treating dilated cardiomyopathy. The patient began taking 25 mg twice daily of carvedilol, as well as 25 mg once daily of eplerenone. However, the patient's condition continued to deteriorate.

In January 2015, the patient underwent an unsuccessful procedure to ablate cardiac tissue causing his PVC burden. His heart ejection fraction (EF), previously measured at 55%, was now measured at 45%. Later that month, the patient was hospitalized for Sotalol (antiarrhythmic drug) initiation. Sotalol was also unsuccessful in treating the patient's PVCs.

After extensive reading, the patient located some fairly obscure evidence that colchicine, an ancient drug typically used to treat gout, might ameliorate disease effects in LMNA cells. To our knowledge, colchicine has never been used in patients with "non-ischemic/LMNA cardiomyopathy," or to reduce "PVC-related cardiomyopathy." After extensive conversation about risks/benefits, Dr. Wilcox initiated colchicine one week after Sotalol proved unsuccessful in treating the patient's PVCs.

Within 48 hours of colchicine administration, the patient's PVC volume diminished considerably. The patient had been very symptomatic with PVC's and could tell when his he was having PVC's. The patient also felt his general condition continued to improve during the following months.

An August 2015 echocardiogram showed a 20% improvement in cardiac output, measured non-invasively, using LVOT velocity time integral (VTI). Further, the patient was now considered to have NYHA class I heart failure symptoms and able to resume all previous activities, including running and biking, whereas previously the patient was NYHA class III (i.e., heart failure symptoms with mild activity).

A February 2016 echocardiogram showed further improvement in cardiac output (i.e., LVOT initially was 15, now measured 22). The patient's heart demonstrated positive ventricular remodeling, including reduction in left ventricular size and volume, and improvement in ejection fraction from 40-45% to 55%.

In March 2016, the patient has ceased taking eplerenone because of elevated potassium levels. As of July 2016, the patient stopped taking Sotalol because it seemed superfluous in respect to the patient's carvedilol regimen, and the patient has continued to be NYHA class I (i.e. asymptomatic). The patient's cardiomyopathy and PVC burden, and overall health has continued to improve, and the patient is training for a half marathon to raise money for laminopathy research.

The patient is currently prescribed 1.8 mg of colchicine twice daily (i.e., 3.6 mg total dose), which far exceeds typical dosing for acute gout (i.e. 0.6 mg twice daily). The patient has not experienced negative side effects from colchicine, and the patient has blood drawn/laboratory data monitored closely for myelosuppression.

Example 3—Microtubule Polymerization Modulators for Treating LMNA-Related Dilated Cardiomyopathy Background and Rationale Dilated Cardiomyopathy (DCM) is often a genetic form of heart disease which occurs when cardiac muscle becomes stretched in a chamber of the heart (left ventricle) causing the chamber to become enlarged or "dilated." The dilated chamber is unable to pump blood as efficiently as a normal-size chamber, and as a result, the cardiac muscle tries to increase the amount of blood being pumped through the heart. This often results in all four chambers of the heart becoming dilated. As the chambers become dilated, the cardiac muscle that forms the chambers becomes increasing thin and weakened and less able to pump blood. Over time, DCM results in heart failure, which is a clinical syndrome that occurs when the heart muscle is weakened and cannot pump enough blood to meet the body's needs for blood and oxygen. A diagnosis of heart failure is associated with high risk of mortality, with average 5 year survival rates of 50% at the time of initial diagnosis.

A patient may have DCM for many years prior to symptoms developing. Symptoms typically begin in mid-adulthood, but may occur at any time from infancy to late adulthood. Symptoms of DCM may include an irregular heartbeat or arrhythmia, shortness of breath or dyspnea, extreme tiredness or fatigue, fainting episodes or syncope, and swelling of extremities such as the legs and feet. In some unfortunate cases, the first sign of DCM is sudden cardiac arrest.

It has been estimated that ~750,000 people in the United States have DCM. Up to half of these cases are inherited/familial DCM, which is a genetic form of the disease. Mutations in more than 30 genes have been found to cause familial DCM, and these genes generally encode proteins that are found in cardiac muscle cells (i.e., cardiomyocytes). Many of these proteins play important roles in the contraction of cardiac muscle through association with cell structures called "sarcomeres," which are the basic units of muscle contraction and comprise proteins that generate the mechanical force needed for muscles to contract. Other proteins associated with familial DCM make up the structural framework or "cytoskeleton" of cardiomyocytes. The remaining proteins associated with familial DCM regulate biological processes within cardiomyocytes to ensure proper functioning.

One gene associated with familial DCM is the lamin A/C gene or "LMNA." The LMNA gene is located on chromosome 1, NC_000001.11 (156082546 . . . 156140089). The LMNA gene provides instructions for making several slightly different proteins called lamins. The two major proteins produced from LMNA are lamin A and lamin C, which are made in most cells of the body. Lamin A is 664 amino acids in length and lamin C is 572 amino acids in length, and lamin A and lamin C are identical from amino acids 1-566.

LMNA-related dilated cardiomyopathy (DCM) is a genetic disorder that is inherited dominantly. It has been estimated that LMNA-related DCM affects at least 80,000 people in the United States alone, although the exact prevalence of LMNA-related DCM is unknown because many patients with DCM do not undergo genetic testing. The natural history of cardiac disease associated with LMNA-related cardiomyopathy is progression, and many patients need a heart transplant or experience sudden cardiac death.

Colchicine as an Exemplary Modulator of Microtubule Polymerization—Description and Intended Use Colchicine is an alkaloid extracted from plants of the genus *Colchicum* and in particular *Colchicum autumnale* or autumn *crocus*. *Colchicum* extracts have been used for many years to treat inflammatory and non-inflammatory conditions.[1]

Colchicine is approved and marketed for treating gout under the tradename "Colcrys™" (Takeda Pharms USA) and a generic version also is available (Prasco Laboratories). Colcrys™ brand colchicine and its generic counterpart are sold as a 0.6 mg coated tablet. The recommended dose of colchicine for treatment of a gout flare is 1.2 mg (two tablets) at the first sign of the flare followed by 0.6 mg (one tablet) one hour later.

In addition to gout, colchicine is used to treat familial Mediterranean fever, pericarditis and Behçet's disease.[2] Familial Mediterranean fever (FMF) is a hereditary autoinflammatory disease, characterized by recurrent bouts of fever, peritonitis, pleuritis, painful, swollen joints and a characteristic ankle rash. Its major complication is the insidious development of secondary (AA) amyloidosis with eventual renal failure in uncontrolled patients. Long-term use of Colchicine has been shown to be very effective for treatment of FMF by preventing attacks, reduction of symptoms and in the prevention and treatment of amyloidosis.[3] The recommended dose of colchicine for treatment of FMF is 1.2-2.4 mg/day orally in single daily dose or divided q12 hr. This dose may be increased in 0.3 mg/day increments as necessary to control disease or decreased in 0.3 mg/day increments if intolerable side effects develop.

In laboratory studies of LMNA cells, colchicine was shown to rescue nuclear shape defects that are characteristic of LMNA cells.[4] Early clinical experience as described herein in Example 2 also suggests a benefit with improvement in cardiac function, reduction in cardiac arrhythmias, and improvement in exercise tolerance when colchicine is administered to a patient having LMNA-related DCM. This project aims to study the effect of colchicine in a broader group of patients with LMNA-related DCM.

Study Design and Objectives

This study is a single-center, non-randomized, prospective, clinical feasibility trial to evaluate the effect of colchicine in a proposed number of up to 15 LMNA cardiomyopathy patients. Patient enrolled in the study will be followed for 12 months.

Aims of the study may include, but are not limited to, studying the effect of colchicine in LMNA cardiomyopathy patients. Objectives of the study may include, but are not limited to: 1) determining the effect of colchicine (i.e., "study drug") on cardiac arrhythmia burden via use of a ZIO® brand monitoring patch; 2) determining the effect of study drug on cardiac structure/remodeling/inflammation via diagnostic imaging (e.g., via use of 3D Echo, cardiac MRI-PET imaging); determining the effect of study drug on cardiac function/remodeling/inflammation via diagnostic imaging (e.g., via laboratory biomarkers); and determining the effect of study drug on cardiovascular limitation to exercise (via cardiopulmonary exercise testing (CPET)).

Study Population

Inclusion criteria for patients in the study include: 1) Age 18 and above; 2) Confirmed diagnoses of LMNA cardiomyopathy (e.g., confirmed with genetic testing); 3) Evidence of myocardial dysfunction OR cardiac arrhythmia as measured by one or more of the following: i) ≤50% left ventricular ejection fraction on echocardiography or cardiac MRI, ii) Evidence of myocardial systolic dysfunction/abnormal cardiac mechanics on echocardiogram [(<20% Global Longitudinal Strain (GLS)], iii) Evidence of interstitial fibrosis or delayed gadolinium enhancement on Cardiac MRI, or iv) Cardiac arrhythmias (either atrial arrhythmias such as atrial fibrillation, atrial tachycardia, etc. or ventricular arrhythmias [(e.g. premature ventricular contractions (PVC) or non-sustained ventricular tachycardia (NSVT), or sustained VT)] as recorded on implantable cardiac devices (ICD, pacemaker) or ZIO brand monitoring patch; and 4) a patient's willingness and ability to comply with scheduled visits, treatment plan, laboratory tests, and other study procedures.

Exclusion criteria for patient in the study include: 1) Patients with cardiomyopathy not due to LMNA mutation; 2) Patients with LMNA mutation and no evidence of myocardial dysfunction or arrhythmia (see inclusion criteria); 3) Women who are pregnant, breastfeeding, or planning to become pregnant; 4) Known or suspected hypersensitivity/allergy to colchicine; 5) Liver disease, cirrhosis of the liver, hepatitis B or C, or significantly abnormal liver function test results (>2 ULN); 6) Any concomitant condition in which, in the opinion of the investigator, would not allow safe participation in the study (e.g., drug addiction, alcohol abuse); 7) Patient with chronic renal insufficiency defined as serum creatinine ≥3 mg/dl (or 265.2 µmol/L), currently on dialysis or in renal failure (estimated Glomerular Filtration Rate [eGFR]<30 mL/min; 8) Clinically significant, untreated coronary artery disease (CAD) (>50% lesions in any coronary artery); 9) Life expectancy less than the expected duration of the trial due to concomitant disease; and 10) Medical indication for long-term use of potent CYP2A3 inhibitors and P-gp inhibitors.

Study Procedures

Screening Evaluations.

After the investigator and research team has determined that a patient meets all of the inclusion criteria, and none of the exclusion criteria, the patient will be asked to consent to participate in the study. Written subject informed consent will be obtained prior to any study-related procedures. At the time of consent staff will interview patients and review necessary medical records. The following information will be reviewed or collected at the time of screening or within 30 days of study enrollment, unless otherwise noted: 1) Sign Informed Consent; 2) Physical exam including vital signs; 3) Medical History, including confirmation of LMNA cardiomyopathy and review of heart failure symptoms; 4) Review and document medications taken in the last 30 days; 5) Blood draw for laboratory tests: Hematology (complete blood count), Comprehensive Metabolic Panel (CMP), creatine kinase (CK), Troponin, N-terminal pro-brain natriuretic peptide (NT-proBNP), ST2 cardiac biomarker, and Galectin-3; 6) Echocardiogram with 3D ejection fraction, chamber quantification and speckle-tracking (strain imaging); 7) Cardiac monitoring via ZIO® brand monitoring patch for a minimum of 48 hours; 8) Six-Minute Walk Test (6MWT); and 9) Cardiopulmonary exercise testing (CPET) if not performed in the last 60 days.

Study Enrollment.

Once eligibility is confirmed subjects will enrolled into the study, assigned a unique study ID and receive study medication as a three week supply of colchicine (0.6 mg, Prasco Laboratories).

Scheduled Follow-Up Visits.

During the titration period subjects will be asked to return every two weeks for safety labs (e.g., CBC, CMP, CK) and in order to study medication titration. Medication compliance, adverse events and current medications will also be reviewed at these visits.

Medication Titration Schedule (Based on Symptoms and Safety Labs)

Week 0 (Enrollment): 0.3 mg daily (0.3 mg (½ tab) in the evening for two weeks (½ pill daily));

Week 2 (Day 14±3 days)—0.3 mg BID (0.3 mg in the morning and 0.3 mg in the evening for two weeks (total daily dose=0.6 mg) (One pill daily));

Week 4 (Day 28±3 days)—0.6 mg BID (0.6 mg in the morning and 0.6 mg in the evening for 2 weeks (total daily dose=1.2 mg) (Two pills daily));

Week 6 (±3 days)—0.9 mg BID (0.9 mg (1½ pill) in the morning and 0.9 mg (1½ pill) in the evening for 2 weeks (total daily dose=1.8 mg) (Three pills daily));

Week 8 (±3 days)—1.2 mg BID (1.2 mg in the morning and 1.2 mg in the evening (total daily dose=2.4 mg) (Four pills daily) Target Dose); and Monthly (±7 days): 1.2 mg BID (4 pills daily).

Permitted Dose Adjustments and Interruptions of Treatment

For patients who are unable to tolerate the protocol-specified dosing scheme, dose level adjustments and interruptions of study treatment are permitted in order to keep the patient on study drug. The following guidelines will be followed.

Dose Reduction Indications.

The dose of study medication may be decreased if any of the following criteria are met: 1) Inability to tolerate drug dose due to diarrhea and/or unable to be managed with lomotil (immodium); 2) Leukopenia: drop in WBC to <3 K/uL; 3) Rise in aspartate aminotransferase (AST)/alanine aminotransferase (ALT) to 2× upper limit of normal (ULN); and 4) Reduction in baseline creatinine clearance by >50%. Study drug will be held for 72 hours, labs will be re-drawn and study drug will be resumed at the dose previously tolerated by the patient. If intolerable side effects continue the dose will be decreased in increments of 0.3 mg.

Stopping Parameters.

Study medication will be stopped if any of the following criteria are met: 1) Inability to tolerate drug dose due to diarrhea and/or unable to be managed with lomotil (immodium); 2) Leukopenia (drop in WBC to <3 K/uL) with lowest dost (0.3 mg QD); 3) Rise in AST/ALT to 2×ULN with lowest dose (0.3 mg QD); and 4) Reduction in creatinine clearance to <30 mL/min. Study drug may be reintroduced in those patients who temporarily discontinue it as soon as medically justified in the opinion of the investigator. Once the investigator considers the patient's condition appropriate for receiving the study drug, the investigator can re-start the patient on the study drug at the most appropriate and allowable dose level.

Study Procedures

Echocardiogram (Strain Imaging).

Echocardiogram with 3D ejection fraction, chamber quantification and speckle-tracking will be performed a baseline and months 3, 6, 9 and 12.

Cardiopulmonary Exercise Testing (CPET).

Cardiopulmonary exercise (CPET) testing will be performed routinely at baseline (clinical CPET performed up to 60 days prior to enrollment is acceptable) and 12 months to assess patients' exercise tolerance. For all CPET tests, patients will be exercised until they have reached a symptom-limited maximal effort.

Respiratory gases will be measured with a standard metabolic cart equipped with $O_2$ and $CO_2$ analyzers. Continuous 12-lead ECG monitoring will be performed during the exercise test. The patient will be exercised on a treadmill and will be exercised to his/her symptomatic maximum. Respiratory gas measurements will be made continuously while the patient exercises. Symptoms experienced by the patient during exercise (e.g., angina, dyspnea, fatigue, dizziness) will be recorded. Following the test, the patient will be observed for at least 15 minutes, or longer as determined by the investigator, before discharge from the laboratory.

Measured Exercise Variables in CPET.

Minute oxygen consumption ($VO_2$; ml/min), minute carbon dioxide production ($VCO_2$; ml/min), and minute ventilation (VE; L/min) will be measured using a breath-by-breath respiratory gas analyzer. Minute oxygen consumption will be normalized for body size by dividing the patient's weight in kg ($VO_2$ in ml/kg/min). Peak oxygen consumption will be that oxygen consumption at peak exercise with respiratory gas exchange ratio greater than 1.0. The anaerobic threshold divided by predicted maximum consumption for age and gender×100 will be calculated to assess for effort. The oxygen consumption divided by the predicted maximum×100 will be calculated to normalize for age and gender. Watts and METS at peak exercise will be a measure of maximum workload, and exercise time will also be recorded.

Six Minute Walk Test (6MWT).

A six-minute walk test (6 MWT) will be performed at baseline and at months 3, 6, 9 and 12. Each patient will be required to undergo a six-minute walk test in accordance with the American Thoracic Society (ATS) Statement on the guidelines for the 6MWT. Patients will be instructed to walk as far as possible at a comfortable pace during a six minute time period. Patients will be instructed that they may get out of breath or become exhausted, that they are permitted to slow down, to stop, and to rest as necessary, that they may lean against the wall while resting, but should resume walking as soon as they are able. Patients will be advised to use their usual walking aids during the test (cane, walker, etc.) and continue their usual medical regimen on the days of the tests. At the conclusion of the six-minute time period, the distance walked will be determined and recorded in meters. Reasons for immediately stopping a 6MWT may include the following: (1) chest pain, (2) intolerable dyspnea, (3) leg cramps, (4) staggering, (5) diaphoresis, and (6) pale or ashen appearance.

Study Medication Risks

Colchicine is known to exhibit negative side-effects such as gastrointestinal disorders and diarrhea. In some embodiments, colchicine may be administered with an ancillary medication that ameliorates and/or prevents gastrointestinal disorders and diarrhea. The following adverse reactions (AEs) have been reported with colchicine. These have been generally reversible upon temporarily interrupting treatment or lowering the dose of colchicine.

Gastrointestinal.

Very common (10% or more): Diarrhea (23%) Common (1% to 10%): Abdominal cramping, abdominal pain, nausea, vomiting Hematologic.

Rare (less than 0.1%): Agranulocytosis, thrombocytopenia, aplastic anemia, leukopenia, granulocytopenia, pancytopenia Nervous System.

Rare (less than 0.1%): Peripheral neuritis, sensory motor neuropathy

Musculoskeletal.

Rare (less than 0.1%): Myopathy, rhabdomyolysis, elevated CPK, myotonia, muscle weakness, muscle pain Respiratory.

Common (1% to 10%): Pharyngolaryngeal pain (3%)

Genitourinary.

Rare (less than 0.1%): Azoospermia, oligospermia

Dermatologic.

Rare (less than 0.1%): Alopecia Very rare (less than 0.01%): Nonthrombocytopenic purpura rashes, rashes, urticaria, dermatitis.

Contraindications

Patients with renal or hepatic impairment should not be given colchicine in conjunction with P-glycoprotein (P-gp) or strong CYP3A4 inhibitors (except fosamprenavir) as follows: atazanavir sulfate (Reyataz); clarithromycin (Biaxin); cyclosporine (Neoral, Gengraf, Sandimmune); darunavir (Prezista); fosamprenavir (Lexiva) with ritonavir; indinavir (Crixivan); itraconazole (Sporanox); ketoconazole (Nizoral); lopinavir/ritonavir (Kaletra); nefazodone (Serzone); nelfinavir mesylate (Viracept); ritonavir (Norvir); saquinavir mesylate (Invirase); telithromycin (Ketek); and tipranavir (Aptivus). In these patients, life-threatening and fatal colchicine toxicity has been reported with colchicine taken in therapeutic doses. Participants will also be instructed to avoid grapefruit juice due to interactions with colchicine. Dose of colchicine will be adjusted per labeling instructions when administered with drugs known to inhibit CYP3A4 and/or P-glycoprotein (P-gp). Participants will be carefully monitored for any signs or symptoms of muscle pain, tenderness, or weakness. Monthly safety labs will be performed to check renal function, CBC and chemistry throughout the study.

CONCLUSION AND BENEFITS

Patients with LMNA-related DCM generally do not respond to existing medical therapy for heart failure and often experience sudden death from cardiac rhythm disorders. The use of colchicine may help treat these non-responding patients and reduce fatality in this population from cardiac rhythm disorders.

Currently, no medication is approved to recover function in hearts affected by LMNA-related DCM or to reduce the burden of arrhythmia in patients with LMNA-related DCM. The proposed study may be utilized to recover heart function and reduce the burden of arrhythmia in patients with LMNA-related DCM.

REFERENCES

1. Vitale A, Rigante D, Lucherini O M, et al; Biological treatments: new weapons in the management of monogenic autoinflammatory disorders. Mediators Inflamm. 2013 2013:939847. doi: 10.1155/2013/939847. Epub 2013 Jul. 21.
2. Cocco, Giuseppe; Chu, David C. C.; Pandolfi, Stefano (2010). "Colchicine in clinical medicine. A guide for internists". European Journal of Internal Medicine. 21 (6): 503-8. PMID 21111934. doi:10.1016/j.ejim.2010.09.010.
3. Goldfinger S E. Colchicine for familial Mediterranean fever. New England Journal of Medicine. 1972; 287(25): p. 1302.
4. Larrieu et al, Chemical Inhibition of NAT10 Corrects Defects of Laminopathic Cells. Science. 2014:344; 527-32.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating lamin A/C (LMNA)-related dilated cardiomyopathy (DCM) in a subject in need thereof, the method comprising administering an effective amount of a modulator of microtubule polymerization.

2. The method of claim 1, wherein the LMNA-related DCM is associated with one or more mutations in LMNA selected from K97E, E111X, E161K, R189W, R190Q, R190W, E203V, K219T, E317K, R644C, a single nucleotide deletion at nucleotide 959, and a four base pair insertion at 1,713 cDNA.

3. The method of claim 1, wherein the LMNA-related DCM is associated with one or more mutations in LMNA that disrupt formation or function of the Links the Nucleus to the Cytoplasm (LINC) complex.

4. The method of claim 1, wherein the subject having lamin A/C (LMNA)-related dilated cardiomyopathy (DCM) is exhibiting a cardiac conduction system disease selected from sinus atrial node disease, atrial dysrhythmias, atrioventricular heart block, ventricular tachyarrhythmias, and combinations thereof, and the method treats the cardiac conduction system disease.

5. The method of claim 1, wherein the modulator of microtubule polymerization is an inhibitor of microtubule modulation.

6. The method of claim 5, wherein the inhibitor of microtubule modulation is selected from the group consisting of colchicine, combretastatins, 2-methoxyestradiol, methoxy benzenesulfonamides (E7010), vinblastine, vincristine, vinflunine, crytophycin 52, halichondrins, dolastatin 10, dolastatin 15, hemiasterlin A, and hemiasterlin B.

7. The method of claim 1, wherein the modulator of microtubule polymerization is an inhibitor of microtubule polymerization that binds tubulin at the colchicine domain.

8. The method of claim 1, wherein the modulator of microtubule polymerization is colchicine or a pharmaceutical salt or solvate thereof.

9. The method of claim 8, wherein the colchicine is administered at a dose of at least about 0.3 mg once daily.

10. The method of claim 8, wherein the colchicine is administered at a dose of at least about 0.3 mg twice daily.

11. The method of claim 8, wherein the colchicine is administered at a dose of at least about 0.6 mg twice daily.

12. The method of claim 8, wherein the colchicine is administered at a dose of at least about 0.9 mg twice daily.

13. The method of claim 8, wherein the colchicine is administered at a dose of at least about 1.2 mg twice daily.

14. The method of claim 8, wherein the colchicine is administered at a dose level within a range of 0.005-0.02 mg/kg body mass once daily.

15. The method of claim 8, wherein the colchicine is administered at a dose level within a range of 0.005-0.02 mg/kg body mass twice daily.

16. The method of claim 1, further comprising administering to the subject an agent selected from the group consisting of an angiotensin converting enzyme (ACE) inhibitor, a beta blocker, an anti-aldosterone agent, and combinations thereof.

17. The method of claim 1, further comprising implanting in the subject an implantable cardioverter-defibrillator (ICD).

\* \* \* \* \*